United States Patent
Govari

(10) Patent No.: US 12,186,013 B2
(45) Date of Patent: *Jan. 7, 2025

(54) DETECTION OF BALLOON CATHETER TISSUE CONTACT USING OPTICAL MEASUREMENT

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/517,833

(22) Filed: Nov. 22, 2023

(65) Prior Publication Data

US 2024/0090944 A1    Mar. 21, 2024

Related U.S. Application Data

(63) Continuation of application No. 17/179,254, filed on Feb. 18, 2021, now Pat. No. 11,849,995.

(51) Int. Cl.
*A61B 18/14* (2006.01)
*A61B 18/00* (2006.01)

(52) U.S. Cl.
CPC ............ *A61B 18/1492* (2013.01); *A61B 2018/00577* (2013.01); *A61B 2018/00982* (2013.01)

(58) Field of Classification Search
CPC ...... A61B 18/1492; A61B 2018/00577; A61B 2018/00982
See application file for complete search history.

(56) References Cited

U.S. PATENT DOCUMENTS

D123,782 S    12/1940  Paul
3,316,896 A    5/1967  Louis
(Continued)

FOREIGN PATENT DOCUMENTS

CN    101422637 A    5/2009
CN    102271607 A    12/2011
(Continued)

OTHER PUBLICATIONS

Extended European Search Report dated Jul. 18, 2022, from corresponding European Application No. 22157169.8.
(Continued)

*Primary Examiner* — Ronald Hupczey, Jr.
*Assistant Examiner* — Abigail Bock

(57) ABSTRACT

A medical system includes a catheter, a light source, a detector, a circulator, and a processor. The catheter includes a distal-end assembly for performing a medical operation on tissue in a cavity of an organ of a patient, the distal-end assembly including an optical fiber configured to guide transmitted light to interact with the tissue of the cavity, and to guide returned light that interacted with the tissue. The light source is configured to produce the transmitted light. The detector is configured to measure the returned light. The circulator is configured to couple the transmitted light from the light source to the optical fiber, and to couple the returned light from the optical fiber to the detector. The processor is configured to identify a contact of the distal-end assembly with the tissue based on the returned light measured by the detector, and to indicate the identified contact to a user.

20 Claims, 4 Drawing Sheets

(56) References Cited

U.S. PATENT DOCUMENTS

| | | |
|---|---|---|
| 4,276,874 A | 7/1981 | Wolvek et al. |
| 4,587,975 A | 5/1986 | Salo et al. |
| 4,709,698 A | 12/1987 | Johnston et al. |
| 4,805,621 A | 2/1989 | Heinze et al. |
| 5,178,957 A | 1/1993 | Kolpe et al. |
| 5,391,199 A | 2/1995 | Ben-Haim |
| 5,429,617 A | 7/1995 | Hammersmark et al. |
| 5,582,609 A | 12/1996 | Swanson et al. |
| 5,584,830 A | 12/1996 | Ladd et al. |
| 5,702,386 A | 12/1997 | Stern et al. |
| 5,718,241 A | 2/1998 | Ben-Haim et al. |
| 5,797,903 A | 8/1998 | Swanson et al. |
| 5,860,974 A | 1/1999 | Abele |
| 5,971,983 A | 10/1999 | Lesh |
| 6,012,457 A | 1/2000 | Lesh |
| 6,024,740 A | 2/2000 | Lesh et al. |
| 6,042,580 A | 3/2000 | Simpson |
| 6,123,718 A | 9/2000 | Tu et al. |
| 6,142,993 A | 11/2000 | Whayne et al. |
| 6,164,283 A | 12/2000 | Lesh |
| 6,171,275 B1 | 1/2001 | Webster, Jr. |
| 6,176,832 B1 | 1/2001 | Habu et al. |
| 6,198,974 B1 | 3/2001 | Webster, Jr. |
| 6,226,542 B1 | 5/2001 | Reisfeld |
| 6,239,724 B1 | 5/2001 | Doron et al. |
| 6,301,496 B1 | 10/2001 | Reisfeld |
| 6,322,558 B1 | 11/2001 | Taylor et al. |
| 6,332,089 B1 | 12/2001 | Acker et al. |
| 6,380,957 B1 | 4/2002 | Banning |
| 6,402,740 B1 | 6/2002 | Ellis et al. |
| D462,389 S | 9/2002 | Provence et al. |
| 6,471,693 B1 | 10/2002 | Carroll et al. |
| 6,484,118 B1 | 11/2002 | Govari |
| 6,522,930 B1 | 2/2003 | Schaer et al. |
| 6,618,612 B1 | 9/2003 | Acker et al. |
| 6,656,174 B1 | 12/2003 | Hegde et al. |
| 6,690,963 B2 | 2/2004 | Ben-Haim et al. |
| 6,814,733 B2 | 11/2004 | Schwartz et al. |
| 6,892,091 B1 | 5/2005 | Ben-Haim et al. |
| 6,893,433 B2 | 5/2005 | Lentz |
| 6,986,744 B1 | 1/2006 | Krivitski |
| 6,987,995 B2 | 1/2006 | Drysen |
| 6,997,924 B2 | 2/2006 | Schwartz et al. |
| 7,142,903 B2 | 11/2006 | Rodriguez et al. |
| 7,156,816 B2 | 1/2007 | Schwartz et al. |
| 7,274,957 B2 | 9/2007 | Drysen |
| 7,340,307 B2 | 3/2008 | Maguire et al. |
| 7,377,906 B2 | 5/2008 | Selkee |
| 7,442,190 B2 | 10/2008 | Abboud et al. |
| 7,536,218 B2 | 5/2009 | Govari et al. |
| 7,591,799 B2 | 9/2009 | Selkee |
| 7,593,760 B2 | 9/2009 | Rodriguez et al. |
| 7,720,517 B2 | 5/2010 | Drysen |
| 7,756,576 B2 | 7/2010 | Levin |
| 7,842,031 B2 | 11/2010 | Abboud et al. |
| 7,853,302 B2 | 12/2010 | Rodriguez et al. |
| 8,000,765 B2 | 8/2011 | Rodriguez et al. |
| 8,021,327 B2 | 9/2011 | Selkee |
| 8,025,661 B2 | 9/2011 | Arnold et al. |
| 8,048,032 B2 | 11/2011 | Root et al. |
| 8,231,617 B2 | 7/2012 | Satake |
| 8,267,932 B2 | 9/2012 | Baxter et al. |
| 8,275,440 B2 | 9/2012 | Rodriguez et al. |
| 8,348,888 B2 | 1/2013 | Selkee |
| 8,357,152 B2 | 1/2013 | Govari et al. |
| D682,289 S | 5/2013 | DiJulio et al. |
| D682,291 S | 5/2013 | Baek et al. |
| 8,456,182 B2 | 6/2013 | Bar-Tal et al. |
| D690,318 S | 9/2013 | Kluttz et al. |
| D694,652 S | 12/2013 | Tompkin |
| 8,641,709 B2 | 2/2014 | Sauvageau et al. |
| 8,721,590 B2 | 5/2014 | Seward et al. |
| 8,777,161 B2 | 7/2014 | Pollock et al. |
| D716,340 S | 10/2014 | Bresin et al. |
| 8,852,181 B2 | 10/2014 | Malecki et al. |
| D720,766 S | 1/2015 | Mandal et al. |
| D721,379 S | 1/2015 | Moon et al. |
| D724,618 S | 3/2015 | Shin |
| 8,998,893 B2 | 4/2015 | Avitall |
| D729,263 S | 5/2015 | Ahn et al. |
| 9,060,756 B2 | 6/2015 | Bencini et al. |
| 9,089,350 B2 | 7/2015 | Willard |
| D736,780 S | 8/2015 | Wang |
| 9,126,023 B1 | 9/2015 | Sahatjian et al. |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| D747,742 S | 1/2016 | Fan et al. |
| D750,644 S | 3/2016 | Bhutani et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,320,631 B2 | 4/2016 | Moore et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| 9,474,486 B2 | 10/2016 | Eliason et al. |
| D783,037 S | 4/2017 | Hariharan et al. |
| 9,655,677 B2 | 5/2017 | Salahieh et al. |
| D791,805 S | 7/2017 | Segars |
| 9,757,180 B2 | 9/2017 | Gelfand et al. |
| 9,795,442 B2 | 10/2017 | Salahieh et al. |
| 9,907,610 B2 | 3/2018 | Beeckler et al. |
| 9,956,035 B2 | 5/2018 | Govari et al. |
| 10,136,945 B2 | 11/2018 | Hettel |
| 10,362,952 B2 | 7/2019 | Basu et al. |
| D861,717 S | 10/2019 | Brekke et al. |
| 10,682,179 B2 | 6/2020 | Ransbury |
| 10,688,278 B2 | 6/2020 | Beeckler et al. |
| 2001/0031961 A1 | 10/2001 | Hooven |
| 2002/0002369 A1 | 1/2002 | Hood |
| 2002/0006455 A1 | 1/2002 | Levine |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | Maguire et al. |
| 2003/0060820 A1 | 3/2003 | Maguire et al. |
| 2003/0120150 A1 | 6/2003 | Govari |
| 2003/0144658 A1 | 7/2003 | Schwartz et al. |
| 2004/0068178 A1 | 4/2004 | Govari |
| 2004/0122445 A1 | 6/2004 | Butler et al. |
| 2004/0147920 A1 | 7/2004 | Keidar |
| 2004/0225285 A1 | 11/2004 | Gibson |
| 2005/0065504 A1 | 3/2005 | Melsky et al. |
| 2005/0070887 A1 | 3/2005 | Taimisto et al. |
| 2005/0096647 A1 | 5/2005 | Steinke et al. |
| 2005/0119686 A1 | 6/2005 | Clubb |
| 2005/0226548 A1 | 10/2005 | Durkin et al. |
| 2006/0013595 A1 | 1/2006 | Trezza et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0270792 A1 | 11/2007 | Hennemann et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0051707 A1 | 2/2008 | Phan et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0249463 A1 | 10/2008 | Pappone et al. |
| 2008/0262489 A1 | 10/2008 | Steinke |

(56) References Cited

U.S. PATENT DOCUMENTS

| | | |
|---|---|---|
| 2008/0281312 A1 | 11/2008 | Werneth et al. |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2010/0041986 A1 | 2/2010 | Nguyen et al. |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0136350 A1 | 5/2012 | Goshgarian et al. |
| 2012/0143177 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0085493 A1 | 4/2013 | Bloom et al. |
| 2013/0090649 A1 | 4/2013 | Smith et al. |
| 2013/0090651 A1 | 4/2013 | Smith |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0197499 A1 | 8/2013 | Lalonde et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | DeBoer et al. |
| 2014/0243821 A1 | 8/2014 | Salahieh et al. |
| 2014/0275993 A1 | 9/2014 | Ballakur |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2015/0005799 A1 | 1/2015 | Lindquist et al. |
| 2015/0011896 A1 | 1/2015 | Yelin et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0196740 A1 | 7/2015 | Mallin et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0256305 A1 | 9/2016 | Longo et al. |
| 2016/0357007 A1 | 12/2016 | Swanson |
| 2016/0374748 A9 | 12/2016 | Salahieh et al. |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312012 A1 | 11/2017 | Harlev et al. |
| 2017/0312022 A1 | 11/2017 | Beeckler et al. |
| 2017/0347896 A1 | 12/2017 | Keyes et al. |
| 2017/0348049 A1 | 12/2017 | Vrba et al. |
| 2018/0074693 A1 | 3/2018 | Jones et al. |
| 2018/0110562 A1 | 4/2018 | Govari et al. |
| 2018/0125575 A1 | 5/2018 | Schwartz et al. |
| 2018/0161093 A1 | 6/2018 | Basu et al. |
| 2018/0256247 A1 | 9/2018 | Govari et al. |
| 2018/0280080 A1 | 10/2018 | Govari et al. |
| 2018/0333162 A1 | 11/2018 | Saab |
| 2018/0368927 A1 | 12/2018 | Lyons et al. |
| 2019/0059818 A1 | 2/2019 | Herrera et al. |
| 2019/0060622 A1 | 2/2019 | Beeckler |
| 2019/0117301 A1 | 4/2019 | Steinke et al. |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0297441 A1 | 9/2019 | Dehe et al. |
| 2019/0298441 A1 | 10/2019 | Clark et al. |
| 2019/0365451 A1 | 12/2019 | Jung, Jr. |
| 2019/0374282 A1 | 12/2019 | Tegg et al. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0155226 A1 | 5/2020 | Valls et al. |
| 2020/0163707 A1 | 5/2020 | Sliwa et al. |
| 2021/0169567 A1 | 6/2021 | Govari et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |
| EP | 0779059 A1 | 6/1997 |
| EP | 1790304 A2 | 5/2007 |
| EP | 2749214 A1 | 7/2014 |
| EP | 2865350 A2 | 4/2015 |
| EP | 2875790 A2 | 5/2015 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3571983 A2 | 11/2019 |
| EP | 3586778 A1 | 1/2020 |
| EP | 3653153 A1 | 5/2020 |
| JP | H06261951 A | 9/1994 |
| JP | H1176233 A | 3/1999 |

(56) References Cited

FOREIGN PATENT DOCUMENTS

| | | | |
|---|---|---|---|
| JP | 2000504242 A | 4/2000 | |
| JP | 2005052424 A | 3/2005 | |
| JP | 2010507404 A | 3/2010 | |
| JP | 2012024156 A | 2/2012 | |
| JP | 2013013726 A | 1/2013 | |
| JP | 2013078587 A | 5/2013 | |
| JP | 2013529109 A | 7/2013 | |
| JP | 2014529419 A | 11/2014 | |
| JP | 2015503365 A | 2/2015 | |
| JP | 2015100706 A | 6/2015 | |
| JP | 2015112113 A | 6/2015 | |
| JP | 2015112114 A | 6/2015 | |
| JP | 2015518776 A | 7/2015 | |
| JP | 2016515442 A | 5/2016 | |
| JP | 2016116863 A | 6/2016 | |
| WO | 9605768 A1 | 2/1996 | |
| WO | 0056237 A2 | 9/2000 | |
| WO | 02102231 A2 | 12/2002 | |
| WO | 2005041748 A2 | 5/2005 | |
| WO | 2008049087 A2 | 4/2008 | |
| WO | 2011143468 A2 | 11/2011 | |
| WO | 2013049601 A2 | 4/2013 | |
| WO | 2013052919 A2 | 4/2013 | |
| WO | 2013154776 A2 | 10/2013 | |
| WO | 2014168987 A1 | 10/2014 | |
| WO | 2015049784 A1 | 4/2015 | |
| WO | 2015200518 A1 | 12/2015 | |
| WO | 2016183337 A2 | 11/2016 | |
| WO | 2016210437 A1 | 12/2016 | |
| WO | 2017024306 A1 | 2/2017 | |
| WO | 2017087549 A1 | 5/2017 | |
| WO | 2018106569 A1 | 6/2018 | |
| WO | 2018129133 A1 | 7/2018 | |
| WO | 2019095020 A1 | 5/2019 | |
| WO | 2021119479 A1 | 6/2021 | |

OTHER PUBLICATIONS

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.
Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.
Co-Pending U.S. Appl. No. 14/578,807, filed Dec. 22, 2014, 21 pages.
Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.
Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.
Extended European Search Report for Application No. EP17168513.4 mailed Sep. 18, 2017, 11 pages.
Extended European Search Report for European Application No. 15201723.2, mailed May 11, 2016, 07 Pages.
Extended European Search Report for European Application No. 17168393.1 mailed Dec. 15, 2017, 12 Pages.
Extended European Search Report for European Application No. 17168518.3, mailed Sep. 20, 2017, 9 Pages.
Extended European Search Report for European Application No. 17173893.3, mailed Nov. 6, 2017, 8 Pages.
Extended European Search Report for European Application No. 17201434.2, mailed Feb. 1, 2018, 10 Pages.
Extended European Search Report for European Application No. 17205876.0, mailed Jun. 1, 2018, 13 Pages.
Extended European Search Report for European Application No. 19177365.4, mailed Nov. 8, 2019, 07 Pages.
Extended European Search Report for European Application No. 19183327.6, mailed Nov. 21, 2019, 8 Pages.
Extended European Search Report for European Application No. 20153872.5, mailed May 7, 2020, 9 Pages.
Extended European Search Report for European Application No. 20195648.9, mailed Feb. 12, 2021, 8 Pages.
Extended European Search Report for European Application No. 21201890.7, mailed Jun. 14, 2022, 14 Pages.
Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.
Haines D.E., et al., "The Promise of Pulsed Field Ablation," Dec. 2019, vol. 19, No. 12, 10 pages.
Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.
International Search Report and Written Opinion for International Application No. PCT/IB2019/052313, mailed Jul. 22, 2019, 8 Pages.
International Search Report and Written Opinion for International Application No. PCT/IB2019/056381, mailed Dec. 17, 2019, 10 pages.
International Search Report and Written Opinion for International Application No. PCT/IB2019/057743, mailed Dec. 6, 2019, 16 Pages.
International Search Report and Written Opinion issued in corresponding International Application No. PCT/IB2019/057742, dated Nov. 28, 2019, 18 Pages.
Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.
Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.
Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.
Partial European Search Report for European Application No. 17168393.1 mailed Sep. 13, 2017, 13 Pages.
Partial European Search Report for European Application No. 17205876.0, mailed Feb. 22, 2018, 10 Pages.
Partial European Search Report for European Application No. 21201890.7, mailed Mar. 14, 2022, 15 Pages.
Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.
Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.
Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QkMWJME].
Youtube: "New Interface TactiCath Contact Force Ablation Catheter," Nov. 26, 2013, 1 Pages, [Retrieved on Nov. 19, 2020], Retrieved from URL: https: /Avww.youtube.com/watch?v=aYvYO8Hpylg].

DETECTION OF BALLOON CATHETER TISSUE CONTACT USING OPTICAL MEASUREMENT

CROSS-REFERENCE TO RELATED APPLICATIONS

The present application is a continuation application of U.S. patent application Ser. No. 17/179,254, filed Feb. 18, 2021, the entire contents of each of which is incorporated herein by reference in its entirety as if fully set forth herein.

FIELD OF THE INVENTION

The present invention relates generally to medical devices, and particularly to methods and systems for detecting contact between a catheter and tissue.

BACKGROUND OF THE INVENTION

Various techniques for verifying catheter contact with tissue were proposed in the patent literature. For example, U.S. Pat. No. 8,025,661 describes a cardiac ablation instrument that includes a catheter body and a tear-shaped balloon connected to the catheter body. The instrument further includes a radiant energy emitter that is axially movable within a central lumen of the catheter body. A radiant energy transparent body surrounds the energy emitter and includes a plurality of illumination fibers disposed circumferentially about the energy emitter. A detector communicates with a contact sensing element and is configured to determine an amount of at least one-color component of the reflected light. The amount of the at least one-color component being indicative of contact between the balloon and a target tissue site.

As another example, U.S. Pat. No. 10,136,945 describes devices and methods for providing and using an ablation catheter. The catheter may include an expandable member having a plurality of electrodes, where each electrode is in association with at least one contact sensor and at least one light emitting element. Light is emitted in response to the contact of the contact sensor with the tissue to be ablated. A light sensor disposed centrally to the catheter gathers light emitted from the light emitting elements and sends a signal to a system controller for display.

U.S. Pat. No. 10,682,179 describes ablation and visualization systems and methods to access quality of contact between a catheter and tissue. In some embodiments, a method for monitoring tissue ablation is provided, that comprises advancing a distal tip of an ablation catheter to a tissue in need of ablation; illuminating the tissue with UV light to excite NADH in the tissue, wherein the tissue is illuminated in a radial direction, an axial direction, or both; determining from a level of NADH fluorescence in the illuminated tissue when the distal tip of the catheter is in contact with the tissue; and delivering ablation energy to the tissue to form a lesion in the tissue.

SUMMARY OF THE INVENTION

An embodiment of the present invention that is described hereinafter provides a medical system including a catheter, a light source, a detector, a circulator, and a processor. The catheter includes a distal-end assembly for performing a medical operation on tissue in a cavity of an organ of a patient, the distal-end assembly including an optical fiber configured to guide transmitted light to interact with the tissue of the cavity, and to guide returned light that interacted with the tissue. The light source is configured to produce the transmitted light. The detector is configured to measure the returned light. The circulator is configured to couple the transmitted light from the light source to the optical fiber, and to couple the returned light from the optical fiber to the detector. The processor is configured to identify a contact of the distal-end assembly with the tissue based on the returned light measured by the detector, and to indicate the identified contact to a user.

In some embodiments, the processor is configured to identify the contact based on a change in measured intensity of the returned light.

In some embodiments, the processor is configured to establish a reference value for the intensity of the returned light while the distal-end assembly is not in contact with the tissue, and to identify the change relative to the reference value.

In an embodiment, a distal end of the fiber includes one of an optical diffusive element and an optical diffractive element, configured to couple the transmitted light from the fiber and couple the returned light that interacted with the tissue into the fiber.

In some embodiments, the optical diffractive element includes an optical grating coupler.

In other embodiments, the distal end of the fiber includes an opaque ending of the fiber. In yet other embodiments, the distal-end assembly includes an expandable transparent membrane.

In an embodiment, the transparent membrane includes multiple ablation electrodes disposed thereon, and wherein the processor is configured to output a recommendation to perform the medical operation with the electrodes based on identifying the contact with the tissue.

In some embodiments, the light source, the detector and the circulator are fitted at the distal-end assembly.

In some embodiments, the light source is a Light Emitting Diode (LED).

There is additionally provided, in accordance with another embodiment of the present invention, a method including inserting a distal-end assembly of a catheter into a cavity of an organ of a patient, for performing a medical operation on tissue in the cavity. Transmitted light is guided in an optical fiber inside the distal-end assembly, to interact with the tissue of the cavity. Returned light that interacted with the tissue is guided via the same optical fiber. A contact of the distal-end assembly with the tissue identified based on the returned light measured by a detector, and the identified contact is indicated to a user.

The present invention will be more fully understood from the following detailed description of the embodiments thereof, taken together with the drawings in which:

DETAILED DESCRIPTION OF EMBODIMENTS

Overview

Figure 1:
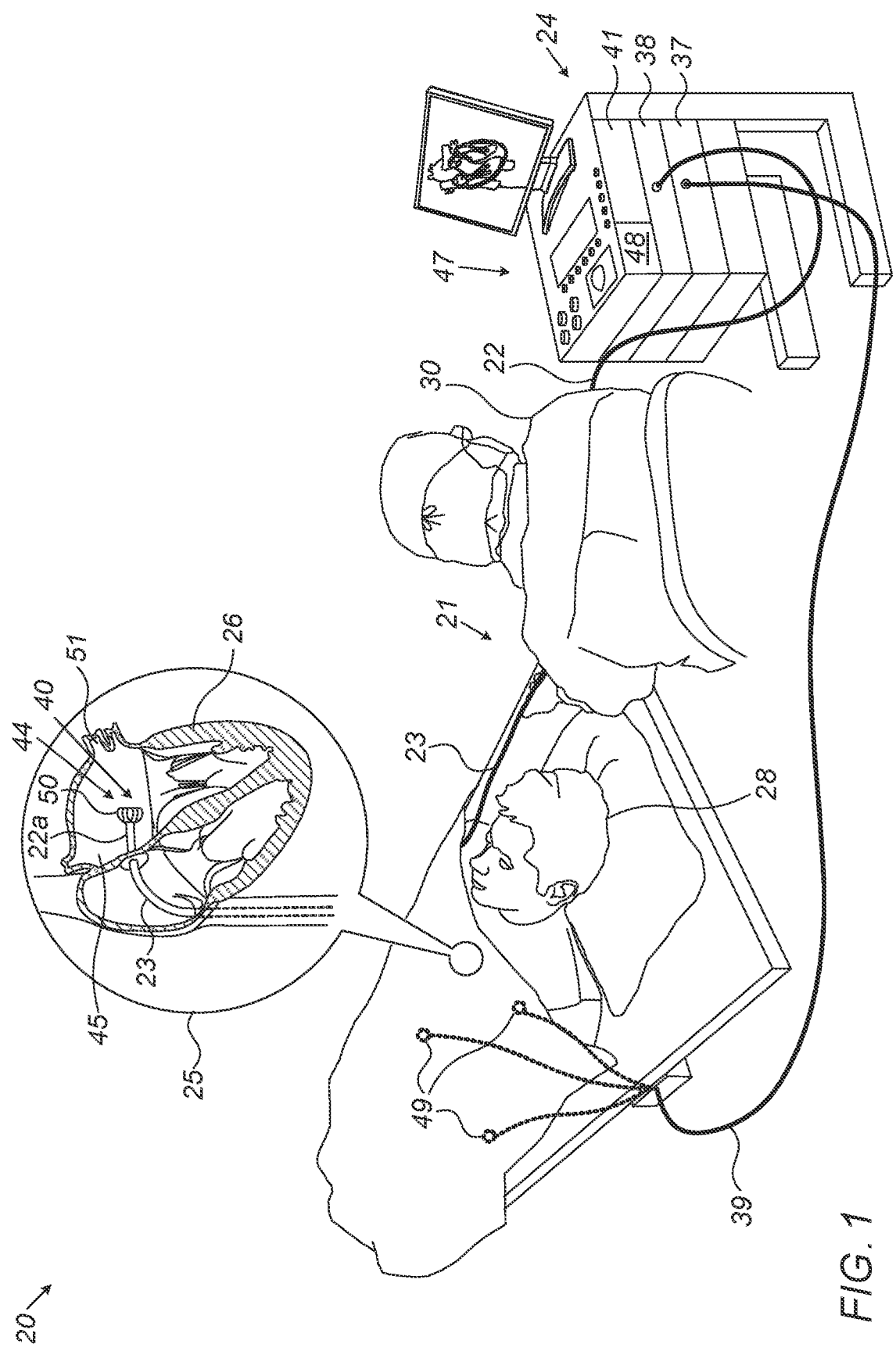
FIG. 1 is a schematic, pictorial illustration of a catheter-based diagnostics and/or ablation system comprising a transparent balloon catheter, in accordance with an embodiment of the present invention.

During a catheterization procedure of an organ of the body, such as cardiac electro-anatomical mapping and/or ablation, there may be a need to verify that electrodes disposed over an expandable membrane coupled to a distal end of a probe, such as a catheter, are in physical contact with wall tissue of a cavity of the organ, such as with a wall tissue of a cardiac chamber.

Embodiments of the present invention that are described hereinafter provide systems in which a distal-end assembly of a catheter includes means to emit light into surrounding media and collect light that interacts with the surrounding media, such as light reflected and/or scattered by a wall tissue of a cavity of the organ.

The disclosed techniques can be used with various distal-end assemblies. For example, the distal-end assembly may comprise an expandable frame, such as used in balloon and basket catheters, or comprise other frames, such as of basket, lasso, multi-arm, and tip catheters. In case of an expandable frame, the distal-end assembly may comprise a transparent expandable membrane (the remainder mostly covered by electrodes, e.g., of a balloon or a basket catheter).

In one embodiment, an optical fiber is installed in the expandable frame and used to transmit light from an external light source, such as a Light Emitting Diode (LED). The same optical fiber is used to convey returned light that interacts with a wall tissue of the cavity to an external detector (e.g., a photodiode). A distal end of the fiber, located inside the transparent expandable membrane of the distal end assembly, comprises a coupler, such as a grating coupler or a diffuser, configured to emit the transmitted light and to couple the returned light into the fiber.

An optical circulator is coupled at the proximal end of the optical fiber to separate the returned light from the transmitted light. The measurement from the detector (e.g., photodiode) is analyzed by a processor to indicate an occurrence of physical contact between the distal-end assembly and the tissue (e.g., by analyzing changes in the intensity of the returned light). The LED, the optical circulator, and the photodiode may be inside an external unit, also called hereinafter "contact detection module."

In another embodiment, the light source, the detector and the circulator are fitted at the distal-end assembly. For example, the LED, the circulator and the photodiode may all be located inside the transparent expandable membrane. In this embodiment, electrical signals are conveyed by a cable running in the catheter's shaft, to drive the LED and to convey measured electrical signals from the photodiode, in the opposite direction, to the processor.

In some embodiments, the processor initially measures the intensity of the returned light when the catheter is in the blood pool but prior to contact of the expanded membrane with tissue, therefore providing a reference value for the intensity. Since the intensity of the returned light changes when the transparent membrane contacts tissue relative to the reference value, the processor uses this change for contact detection.

In an embodiment, a system is provided that includes (a) a catheter, comprising a distal-end assembly for performing a medical operation on tissue in a cavity of an organ of a patient, the distal-end assembly comprising an optical fiber configured to guide transmitted light to interact with the tissue of the cavity, and to return returned light that interacted with the tissue, (b) a light source configured to produce the transmitted light, (c) a detector configured to measure the returned light, (d) a circulator configured to couple the transmitted light from the light source to the optical fiber, and to couple the returned light from the optical fiber to the detector, and (e) a processor, configured to identify a contact of the distal-end assembly with the tissue based on the returned light measured by the detector, and to indicate the identified contact to a user.

By offering a single optical-fiber-based tissue contact detection, a balloon catheter can be made with smaller diameter, allowing better flexibility of the shaft, and improved maneuverability, and therefore enable improved access to some target body locations.

System Description

FIG. 1 is a schematic, pictorial illustration of a catheter-based diagnostics and/or ablation system 20 comprising a transparent balloon catheter 40, in accordance with an embodiment of the present invention. System 20 comprises a catheter 21, wherein a shaft 22 of the catheter is inserted by a physician 30 through the vascular system of a patient 28 through a sheath 23. The physician then navigates a distal end 22a of shaft 22 to a target location inside a heart 26 of the patient.

In the embodiment described herein, catheter 21 may be used for any suitable diagnostic and/or therapeutic purpose, such as electrophysiological sensing and/or irreversible electroporation (IRE) and/or radiofrequency (RF) ablation to electro-physiologically isolate a PV ostium 51 tissue in left atrium 45 of heart 26.

Once distal end 22a of shaft 22 has reached the target location, physician 30 retracts sheath 23 and expands balloon 40, typically by pumping saline into balloon 40. Physician 30 then manipulates shaft 22 such that electrodes 50 disposed on the balloon 40 catheter engage an interior wall of a PV ostium 51 to perform electrophysiological sensing, and/or apply IRE and/or RF ablation via electrodes 50 to ostium 51 tissue.

Figure 2:
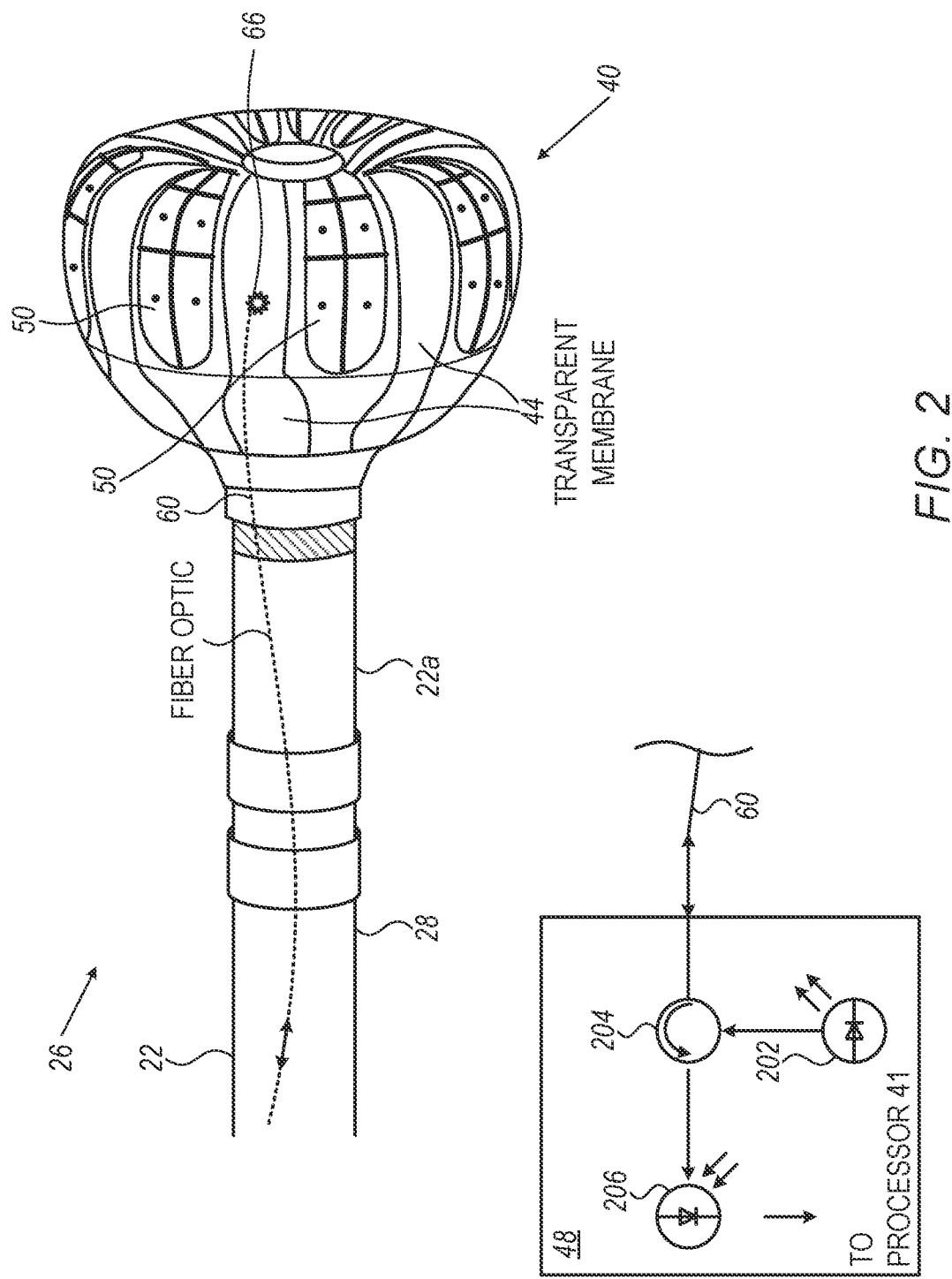
FIG. 2 is a schematic, pictorial illustration of the transparent balloon catheter and of the contact detection module of FIG. 1, in accordance with an embodiment of the invention.

As seen in inset 25, and in more detail in FIG. 2, expandable balloon 40 comprises multiple equidistant smooth-edge electrodes 50. A transparent membrane 44 of balloon 40 enables optical detection of contact with tissue, as described in FIG. 2. Due to the flattened shape of the distal portion of balloon 40, the distance between adjacent electrodes 50 remains approximately constant even where electrodes 50 cover the distal portion. Balloon 40 configuration, when used for IRE, therefore allows more effective electroporation (e.g., with approximately uniform electric field strength) between adjacent electrodes 50 while the smooth edges of electrodes 50 minimize unwanted thermal effects.

In the context of the present disclosure and in the claims, the term "approximately" for any numerical values or ranges indicates a suitable dimensional tolerance that allows the part or collection of components to function for its intended purpose as described herein.

The proximal end of catheter 21 is connected to a console 24 comprising an IRE pulse generator 38 configured to apply the IRE pulses between adjacent electrodes 50. The electrodes are connected to IRE pulse generator 38 by electrical wiring running in shaft 22 of catheter 21. An optical tissue-contact detection module 48 of console 24 is used with balloon 40, as described in FIG. 2.

An optical fiber (seen in FIG. 2) runs inside shaft 22 and is coupled at its proximal end to module 48. A distal end of the fiber includes a coupler (seen in FIG. 2) to emit the transmitted light and to couple the return light into the fiber.

Console 24 comprises a processor 41, typically a general-purpose computer, with suitable front end and interface circuits 37 for receiving signals from catheter 21 and from external electrodes 49, which are typically placed around the chest of patient 28. For this purpose, processor 41 is connected to external electrodes 49 by wires running through a cable 39.

During a procedure, system 20 can track the respective locations of electrodes 50 inside heart 26, using the Active Current Location (ACL) method, provided by Biosense-Webster (Irvine California), which is described in U.S. Pat. No. 8,456,182, whose disclosure is incorporated herein by reference.

In other embodiments, physician 30 can modify, from a user interface 47, any of the parameters, such as a wavelength, used by module 48. User interface 47 may comprise any suitable type of input device, e.g., a keyboard, a mouse, a trackball, among others.

Processor 41 is typically programmed in software to carry out the functions described herein, including analyzing signals acquired by module 48, to indicate an occurrence of membrane 44 contact with tissue. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm as disclosed herein, including in FIG. 4, which enables processor 41 to perform the disclosed steps, as further described below.

Detecting Tissue Contact with a Balloon Catheter Using Optical Measurements

FIG. 2 is a schematic, pictorial illustration of transparent balloon catheter 40 and of the contact detection module 48 of FIG. 1, in accordance with an embodiment of the invention. The description below refers to balloon 40, but the techniques described below may be applied, mutatis mutandis, to any catheter having other types of expandable frames, such as, but not limited to, a basket catheter.

Balloon 40 comprises transparent membrane 44 with electrodes 50 disposed on the surface of membrane 44. In some embodiments, when placed in contact with tissue of heart 26, electrodes 50 are configured to sense intra-cardiac electrical signals from the tissue and/or to ablate tissue.

In some embodiments, electrodes 50 are configured to apply, to the tissue, ablation pulses received from IRE generator 38 and controlled by processor 41 and/or by physician 30, as described in FIG. 1 above.

In the shown embodiment, catheter 40 further comprises an optical fiber 60, which runs in shaft 22 and ends within the internal volume of balloon 40 with an optical coupler 66. Light emitted by coupler 66 propagates inside a saline solution used for inflating balloon 40 and interacts with media external to membrane 44, such as with blood and/or wall tissue (seen in FIG. 1).

The light emitted by coupler 66 is generated by an optical source (e.g., an LED) 202 inside unit 48, and transmitted to fiber 60 using a circulator 204. A return light is transmitted by circulator 204 to a photodetector 206. Using a circulator therefore provides separation of the incident light from the return light, which enables the detection of changes, even slight ones, in the intensity of the return light, due to physical contact of transparent membrane 44 with wall tissue.

Returned light measured by photodetector 206 are conveyed as an electrical signal to processor 41 for the processor to perform the analysis required to determine the occurrence of the membrane contact with wall tissue, as described above.

The configuration shown in FIG. 2 is provided by way of example. The principles described herein may similarly be applied to other types of ablation catheters, such as a basket-type distal end having a transparent membrane fitted to its expandable frame. Various types of couplers, such as those corrugated to emit in several directions, or having surface roughness to scatter light, may also be used.

A Balloon Catheter Using an Optical Grating Coupler

Figure 3:
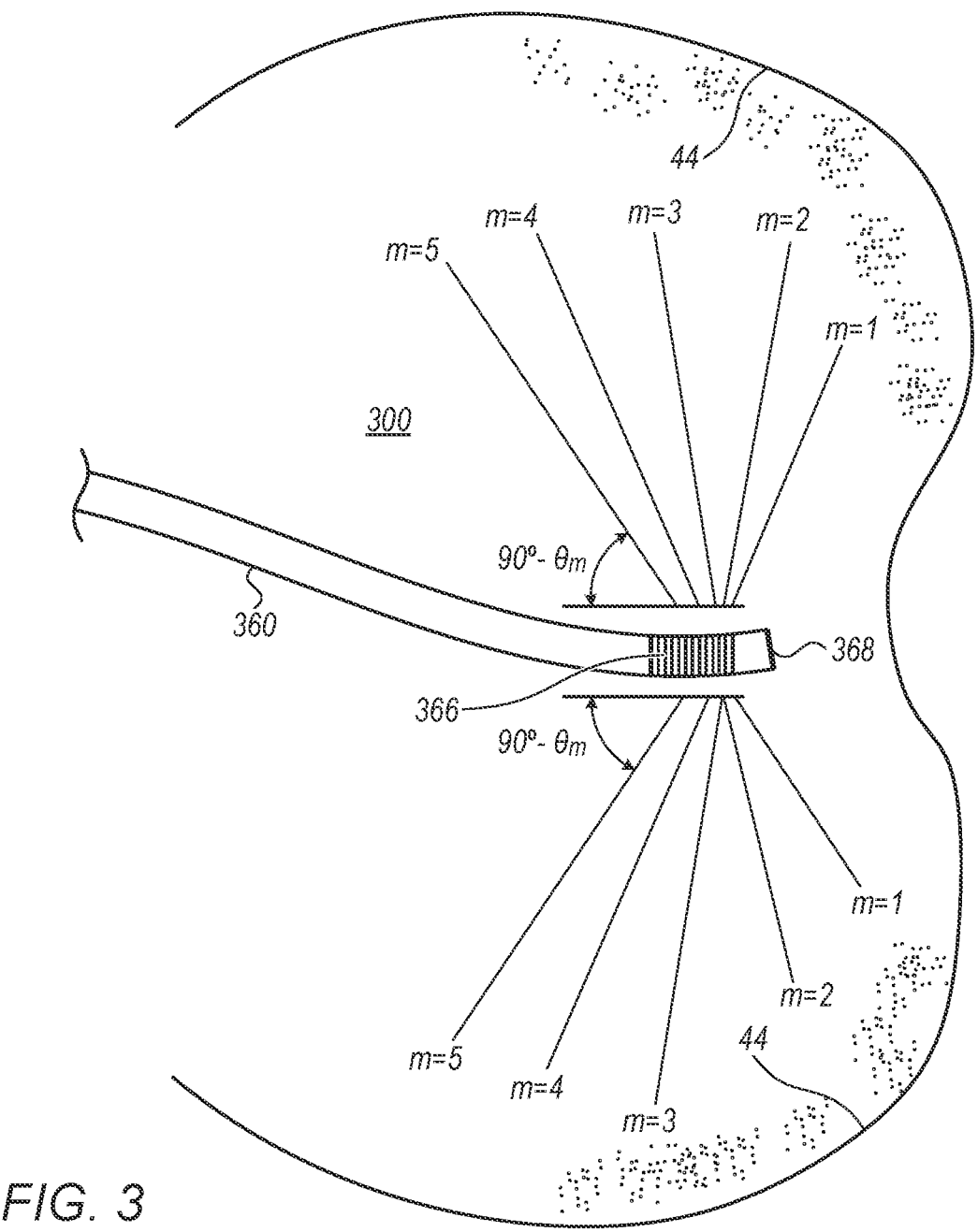
FIG. 3 is a schematic, pictorial illustration of a fiber grating coupler inside the transparent membrane of the balloon catheter of FIG. 1, in accordance with an embodiment of the invention.

FIG. 3 is a schematic, pictorial illustration of a fiber grating coupler 366 inside transparent membrane 44 of balloon catheter 40 of FIG. 1, in accordance with an embodiment of the invention. As seen, coupler 366 is patterned on optical fiber 360 at a distal end of fiber 360, with fiber 360 ending with an opaque termination, to minimize a reflected light.

Proper selection of coupler 366 parameters can make it highly efficient. Specifically, the coupling coefficient of the grating can be maximized by adjusting the groves and length of the grating. In this way, a substantial fraction (e.g., >30%) of the incident light intensity can be coupled out to interact with surrounding media.

Directions at which light is coupled by coupler 366 out into a surrounding media 300, and from which interacted light is coupled back into fiber 360, are defined with angles $\theta_m$ given by the grating equation:

$$\sin(\theta_m) = \frac{1}{n_0}\left(n_{\text{eff}} - \frac{m\lambda_0}{\Lambda}\right), m = 1, 2, 3 \ldots$$

where $n_0$ is the media refractive index (e.g., $n_0$ is approximately 1.33 for saline solution media), $n_{\text{eff}}$ is the effective refraction index (e.g., approximately 1.5) of the fiber guided light of peak intensity wavelength $\lambda_0$ (e.g., 630 nm red light), and $\Lambda$ is the period of the grating (e.g., several microns). Selecting $\Lambda \gg \lambda_0$ ensures that there are many diffraction orders that cover a wide area of the membrane. Alternatively, a smaller period $\Lambda$ (e.g., $\Lambda \geq \lambda_0$) may be selected, to cover, for example, with few diffraction orders, a selected perimeter strip of the membrane where contact determination is most important.

The configuration shown in FIG. 3 is provided by way of example. Other embodiments may induce more uniform emission of light over membrane 44 in other ways (e.g. a multiperiod grating or roughening).

Figure 4:
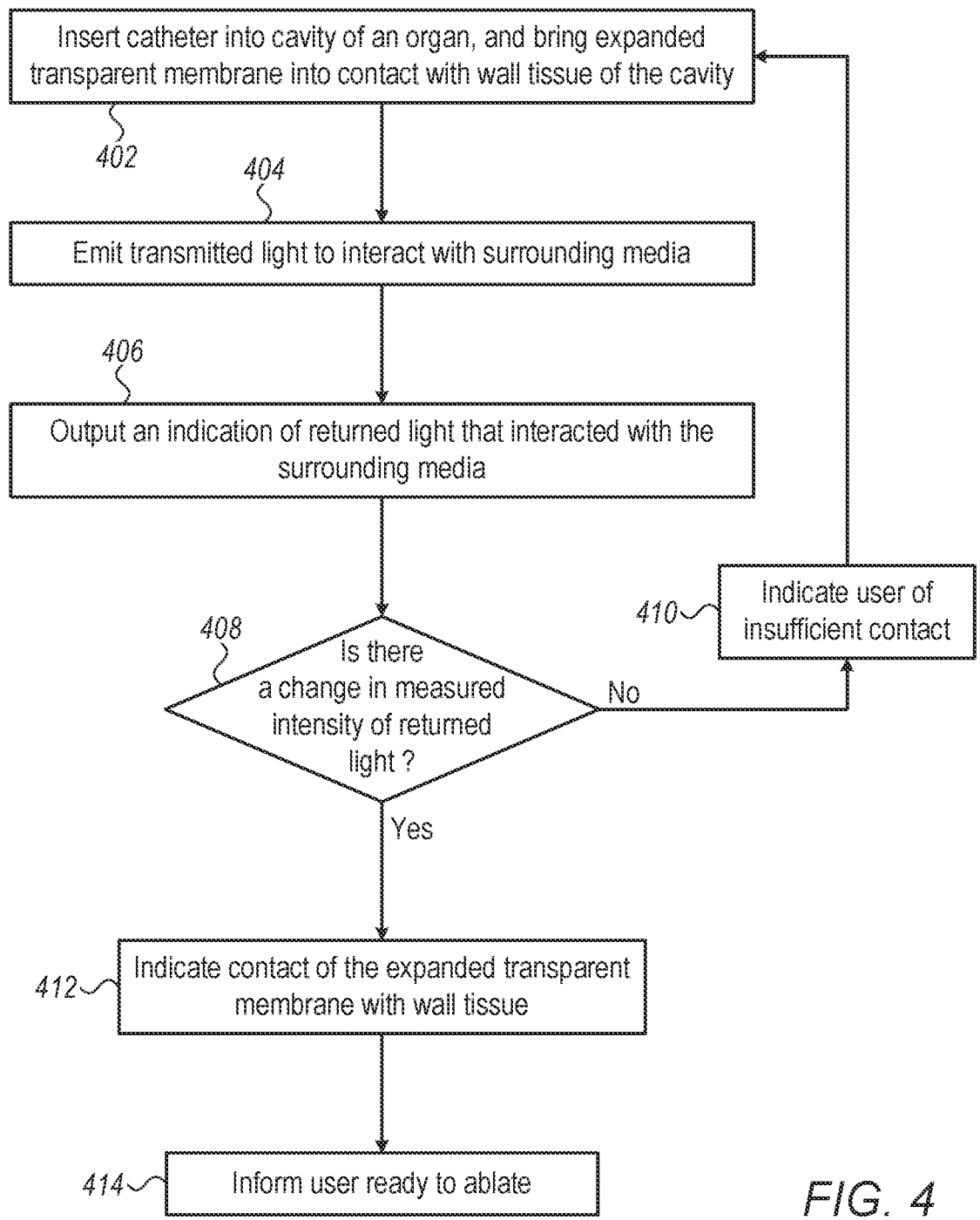
FIG. 4 is a flow chart that schematically illustrates a method for detecting tissue contact with the transparent balloon catheter of FIG. 1, in accordance with an embodiment of the present invention.

Method of Detecting Tissue Contact with a Balloon Catheter Using Optical Measurement FIG. 4 is a flow chart that schematically illustrates a method for detecting tissue contact with transparent balloon catheter 40 of FIG. 1, in accordance with an embodiment of the present invention. The algorithm, according to the presented embodiment, carries out a process that begins when physician 30 navigates balloon catheter 40 to a target tissue location in an organ of a patient, such as at PV ostium 51, using, for example, electrodes 50 as ACL sensing electrodes, and bringing membrane 44 of expanded balloon 40 into contact with ostium tissue, at catheter placement step 402.

In the process, unit 48 transmits light, which is emitted inside the cavity using coupler 360 (seen in FIG. 3), to interact with surrounding media, possibly including wall tissue in contact with membrane 44, at transmitted light emission step 404.

At an acquisition step 406, unit 48 acquires and measures a return light from surrounding media, possibly including wall tissue in contact with membrane 44. At a checking step 408, processor 41 checks if a change of intensity of the return light occurred, e.g., to a degree indicative of a contact.

If the answer is no, the processor issues an indication of insufficient contact made with wall tissue (410), for example as a textual message on a display, and the process returns to step 402.

If the answer is yes, the processor issues an indication of a sufficient contact made with wall tissue (412). In an optional embodiment, the processer may further issue a notice that the balloon is in position for ablation (414).

Although the embodiments described herein mainly address cardiac applications, the methods and systems described herein can also be used in other medical applications, such as in neurology and otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:
  a catheter, comprising a distal-end assembly for performing a medical operation on tissue in a cavity of an organ of a patient, the distal-end assembly comprising an optical fiber configured to guide transmitted light to interact with the tissue of the cavity, and to guide returned light that interacted with the tissue;
  a light source fitted at the distal-end assembly and configured to produce the transmitted light;
  a detector fitted at the distal-end assembly and configured to measure the returned light;
  a circulator fitted at the distal-end assembly and configured to couple the transmitted light from the light source to the optical fiber, and to couple the returned light from the optical fiber to the detector; and
  a processor, configured to identify a contact of the distal-end assembly with the tissue based on the returned light measured by the detector, and to indicate the identified contact to a user.

2. The medical system according to claim 1, wherein the processor is configured to identify the contact based on a change in measured intensity of the returned light.

3. The medical system according to claim 2, wherein the processor is configured to establish a reference value for the measured intensity of the returned light while the distal-end assembly is not in contact with the tissue, and to identify the change relative to the reference value.

4. The medical system according to claim 1, wherein a distal end of the optical fiber comprises one of an optical diffusive element and an optical diffractive element, configured to couple the transmitted light from the fiber and couple the returned light that interacted with the tissue into the optical fiber.

5. The medical system according to claim 4, wherein the optical diffractive element comprises an optical grating coupler.

6. The medical system according to claim 5, wherein a distal end of the optical fiber, comprising the optical grating coupler, is disposed inside an expandable transparent membrane.

7. The medical system according to claim 4, wherein the distal end of the fiber comprises an opaque ending of the fiber.

8. The medical system according to claim 1, wherein the distal-end assembly comprises an expandable transparent membrane.

9. The medical system according to claim 8, wherein the transparent membrane comprises multiple ablation electrodes disposed thereon, and wherein the processor is configured to output a recommendation to perform the medical operation with the electrodes based on identifying the contact with the tissue.

10. The medical system according to claim 8, wherein the light source, the detector, and the circulator are each disposed inside the expandable transparent membrane.

11. A medical system, comprising:
  a transparent expandable membrane disposed at a distal end of a tube, the transparent expandable membrane comprising electrodes disposed thereon configured to deliver ablative energy to tissue in a cavity of an organ of a patient, the transparent expandable membrane further comprising an optical fiber configured to guide transmitted light to interact with the tissue of the cavity, and to guide returned light that interacted with the tissue;
  a light source configured to produce the transmitted light;
  a detector configured to measure the returned light;
  a circulator configured to couple the transmitted light from the light source to the optical fiber, and to couple the returned light from the optical fiber to the detector; and
  a processor, configured to:
    identify a contact of the transparent expandable membrane with the tissue based on the returned light measured by the detector, and to indicate the identified contact to a user; and
    output a recommendation to deliver ablative energy to tissue with the electrodes based on identifying the contact with the tissue.

12. The medical system according to claim 11, wherein the processor is configured to identify the contact based on a change in measured intensity of the returned light.

13. The medical system according to claim 12, wherein the processor is configured to establish a reference value for the measured intensity of the returned light while the transparent expandable membrane is not in contact with the tissue, and to identify the change relative to the reference value.

14. The medical system according to claim 11, wherein a distal end of the optical fiber comprises one of an optical diffusive element and an optical diffractive element, configured to couple the transmitted light from the fiber and couple the returned light that interacted with the tissue into the optical fiber.

15. The medical system according to claim 11, wherein the light source, the detector, and the circulator are each disposed inside the expandable transparent membrane.

16. A medical system, comprising:
- a transparent expandable membrane disposed at a distal end of a tube for performing a medical operation on tissue in a cavity of an organ of a patient, the transparent expandable membrane further comprising an optical fiber configured to guide transmitted light to interact with the tissue of the cavity, and to guide returned light that interacted with the tissue;
- a light source disposed at least partially in the transparent expandable membrane and configured to produce the transmitted light;
- a detector disposed at least partially in the transparent expandable membrane and configured to measure the returned light;
- a circulator disposed at least partially in the transparent expandable membrane and configured to couple the transmitted light from the light source to the optical fiber, and to couple the returned light from the optical fiber to the detector; and
- a processor, configured to identify a contact of the transparent expandable membrane with the tissue based on the returned light measured by the detector, and to indicate the identified contact to a user.

17. The medical system according to claim 16, wherein the processor is configured to identify the contact based on a change in measured intensity of the returned light.

18. The medical system according to claim 17, wherein the processor is configured to establish a reference value for the measured intensity of the returned light while the transparent expandable membrane is not in contact with the tissue, and to identify the change relative to the reference value.

19. The medical system according to claim 16, wherein a distal end of the optical fiber comprises one of an optical diffusive element and an optical diffractive element, configured to couple the transmitted light from the fiber and couple the returned light that interacted with the tissue into the optical fiber.

20. The medical system according to claim 16, wherein the transparent expandable membrane comprises multiple ablation electrodes disposed thereon, and wherein the processor is configured to output a recommendation to perform the medical operation with the electrodes based on identifying the contact with the tissue.

* * * * *